United States Patent [19]
Müller et al.

[11] Patent Number: 6,114,378
[45] Date of Patent: Sep. 5, 2000

[54] FUNGICIDE MIXTURES

[75] Inventors: Ruth Müller, Friedelsheim; Herbert Bayer; Hubert Sauter, both of Mannheim; Eberhard Ammermann, Heppenheim; Gisela Lorenz, Hambach; Siegfried Strathmann, Limburgerhof; Klaus Schelberger, Gönnheim; Maria Scherer, Landau, all of Germany

[73] Assignee: BASF Aktiengesellschaft, Ludwigshafen, Germany

[21] Appl. No.: 09/171,522

[22] PCT Filed: Apr. 23, 1997

[86] PCT No.: PCT/EP97/02046

§ 371 Date: Oct. 21, 1998

§ 102(e) Date: Oct. 21, 1998

[87] PCT Pub. No.: WO97/40677

PCT Pub. Date: Nov. 6, 1997

[30] Foreign Application Priority Data

| Apr. 26, 1996 | [DE] | Germany | 196 16 683 |
| Apr. 26, 1996 | [DE] | Germany | 196 16 685 |
| Apr. 29, 1996 | [DE] | Germany | 196 17 072 |
| Sep. 2, 1996 | [DE] | Germany | 196 35 509 |
| Sep. 2, 1996 | [DE] | Germany | 196 35 517 |
| Sep. 2, 1996 | [DE] | Germany | 196 35 514 |

[51] Int. Cl.⁷ .......... A01N 47/10; A01N 37/12; A01N 37/34; A01N 37/44; A01N 37/52

[52] U.S. Cl. .......... 514/491; 514/476; 514/508; 514/538; 514/539; 514/617; 514/618; 514/619; 514/594

[58] Field of Search .......... 514/508, 476, 514/491, 522, 538, 539, 617, 618, 619, 594

[56] References Cited

U.S. PATENT DOCUMENTS

| 2,457,674 | 12/1948 | Heuberger | 167/22 |
| 2,504,404 | 4/1950 | Flenner | 167/22 |
| 3,379,610 | 4/1968 | Lyon et al. | 167/22 |
| 3,957,847 | 5/1976 | Davidson | 260/465.4 |

FOREIGN PATENT DOCUMENTS

| 95/15083 | 6/1995 | WIPO . |
| 9521154 | 8/1995 | WIPO . |
| 97/00011 | 1/1997 | WIPO . |

OTHER PUBLICATIONS

Research Disclosure (1993) Apr., No. 348.
Pesticide Sci., Bd. 44, N4. 1, May 1995, S. 77–79.

*Primary Examiner*—Allen J. Robinson
*Attorney, Agent, or Firm*—Keil & Weinkauf

[57] ABSTRACT

A fungicidal mixture comprising
 a) an oxime ether of the formula I

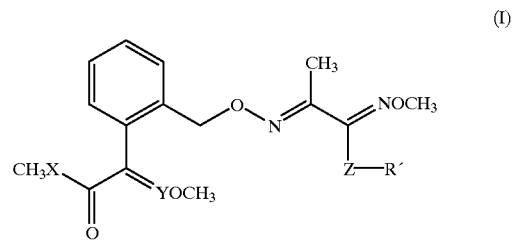

(I)

where the substituents have the following meaning:
X is oxygen or amino (NH);
Y is CH or N;
Z is oxygen, sulfur, amino (NH) or $C_1$–$C_4$-alkylamino (N—$C_1$–$C_4$-alkyl);
R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or benzyl which may be partially or fully halogenated and/or may carry one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

and
 b) a dithiocarbamate (II) selected from the group consisting of
  manganese ethylenebis(dithiocarbamate) (zinc complex) (IIa),
  manganese ethylenebis(dithiocarbamate) (IIb),
  zinc ammoniate ethylenebis(dithiocarbamate) (IIc) and
  zinc ethylenebis(dithiocarbamate) (IId) and/or
 c) 1-(2-cyano-2-methoxyiminoacetyl)-3-ethylurea (III)

$$H_3CCH_2—NHCONH—C(CN)=NOCH_3 \quad (III)$$

in a synergistically active amount.

20 Claims, No Drawings

FUNGICIDE MIXTURES

This application is 371 of PCT/EP97/62046, filed Apr. 23, 1997.

The present invention relates to a fungicidal mixture which comprises a) an oxime ether of the formula I

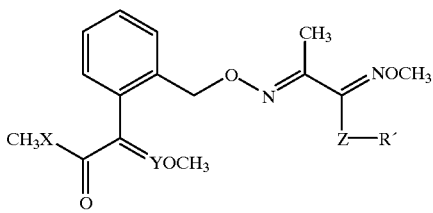

where the substituents have the following meaning:
X is oxygen or amino (NH);
Y is CH or N;
Z is oxygen, sulfur, amino (NH) or $C_1$–$C_4$-alkylamino (N—$C_1$–$C_4$-alkyl);
R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or benzyl which may be partially or fully halogenated and/or may carry one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

and b) a dithiocarbamate (II) selected from the group consisting of
manganese ethylenebis(dithiocarbamate) (zinc complex) (IIa),
manganese ethylenebis(dithiocarbamate) (IIb),
zinc ammoniate ethylenebis(dithiocarbamate) (IIc) and
zinc ethylenebis(dithiocarbamate) (IId), and/or c) 1-(2-cyano-2-methoxyiminoacetyl)-3-ethylurea (III)

in a synergistically active amount.

Moreover, the invention relates to methods of controlling harmful fungi using mixtures of the compounds I, II and/or III and to the use of the compounds I, II and III for the preparation of such mixtures.

The compounds of the formula I, their preparation and their action against harmful fungi are disclosed in the literature (WO-A 95/21,153, WO-A 95/21,154, DE 195 28 651.0).

Also disclosed are the dithiocarbamates II (IIa: common name: mancozeb, U.S. Pat. No. 3,379,610; IIb: common name: maneb, U.S. Pat. No. 2,504,404; IIc: former common name: metiram, U.S. Pat. No. 3,248,400; IId: common name: zineb, U.S. Pat. No. 2,457,674), their preparation, and their action against harmful fungi.

Also disclosed is the compound III (U.S. Pat. No. 3,957,847; common name: cymoxanil), its preparation and its action against harmful fungi.

It is an object of the present invention to provide mixtures which have an improved action against harmful fungi combined with a reduced total amount of active ingredients applied (synergistic mixtures), with a view to reducing the rates of application and to improving the spectrum of action of the known compounds.

We have found that this object is achieved by the mixtures defined at the outset. Moreover, we have found that better control of the harmful fungi is possible by applying the compound I, II and/or III simultaneously together or separately or by applying the compound I, II and III in succession than when the individual compounds are used.

The present invention relates to mixtures of compounds I and II or I and III and mixtures which comprise a compound I, a compound II and a compound III.

The general formula I represents in particular oxime ethers where X is oxygen and Y is CH or where X is amino and Y is N.

Furthermore, preference is given to compounds I where Z is oxygen.

Likewise, preference is given to compounds I where R' is alkyl or benzyl.

With a view to their use in the synergistic mixtures according to the invention, compounds I which are particularly preferred are those listed in the tables below:

Table 1.

Compounds of the formula IA where for each compound ZR' corresponds to one line in Table A

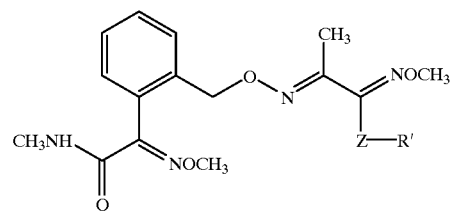

Table 2.

Compounds of the formula IB, where for each compound ZR' corresponds to one line in Table A

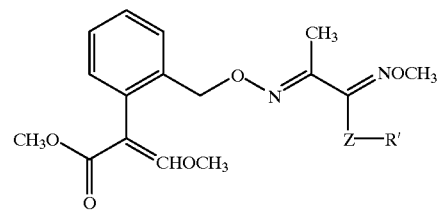

TABLE A

| No. | ZR' |
| --- | --- |
| I.1 | O—$CH_2CH_2CH_3$ |
| I.2 | O—$CH(CH_3)_2$ |
| I.3 | O—$CH_2CH_2CH_2CH_3$ |
| I.4 | O—CH ($CH_3$)$CH_2CH_3$ |
| I.5 | O—$CH_2CH(CH_3)_2$ |
| I.6 | O—$C(CH_3)_3$ |
| I.7 | S—$C(CH_3)_3$ |
| I.8 | O—$CH(CH_3)CH_2CH_2CH_3$ |
| I.9 | O—$CH_2C(CH_3)_3$ |
| I.10 | O—$CH_2C(Cl)$=$CCl_2$ |
| I.11 | O—$CH_2CH$=CH-Cl (trans) |
| I.12 | O—$CH_2C(CH_3)$=$CH_2$ |
| I.13 | O—$CH_2$-(cyclopropyl) |
| I.14 | O—$CH_2$—$C_6H_5$ |
| I.15 | O—$CH_2$-[4-F—$C_6H_4$] |
| I.16 | O—$CH_2CH_3$ |
| I.17 | O—$CH(CH_2CH_3)_2$ |

In relation to the C=Y double bond, the compounds of the formula I can be present in the E or the Z configuration (in relation to the carboxylic acid function). Accordingly, they can be used in the mixture according to the invention in each case either in the form of a pure E or Z isomer or else in the form of an E/Z isomer mixture. The E/Z isomer mixture or the E isomer is preferably used, the E isomer being especially preferred.

The C=N double bonds of the oxime ether groups in the side chain of the compounds I can exist in each case in the form of pure E or Z isomers or in the form of E/Z isomer mixtures. The compounds I can be used in the mixtures according to the invention as isomer mixtures or else as the pure isomers. With a view to their use, compounds I which are particularly preferred are those where the terminal oxime ether group of the side chain is in the cis configuration ($OCH_3$ group to ZR').

Due to their basic character, the compounds I and III are capable of forming adducts or salts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which have attached to them one or two sulfo groups), alkylphosphonic acids (phosphonic acids having straight-chain or branched alkyl radicals of 1 to 20 carbon atoms), arylphosphonic acids or aryldi-phosphonic acids (aromatic radicals, such as phenyl and naphthyl, which have attached to them one or two phosphoric acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the second main group, in particular calcium and magnesium, of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can exist in the various valencies which they can assume.

When preparing the mixtures, it is preferred to employ the pure active ingredients I and II or III, to which further active ingredients against harmful fungi or other pests, such as insects, arachnids or nematodes, or else herbicidal or growth-regulating active ingredients or fertilizers can be admixed, if so required.

The mixtures of the compounds I, II and III, or the simultaneous joint or separate use of the compounds I, II and III, are distinguished by outstanding action against a wide spectrum of phytopathogenic fungi, in particular from the classes of the Ascomycetes, Deuteromycetes, Phycomycetes and Basidiomycetes. Some of them act systemically and can therefore be employed as foliar and soil-acting fungicides.

They are especially important for controlling a large number of fungi in a variety of crop plants, such as cotton, vegetable species (eg. cucumbers, beans and cucurbits), barley, grass, oats, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, Pseudoperonospora species in cucurbits and hops, *Plasmopara viticola* in grapevines, Alternaria species in vegetables and fruit, and Fusarium and Verticillium species.

Furthermore, they can be used in the protection of materials (eg. in the protection of wood), for example against *Paecilomyces variotii*.

The compounds I, II and/or III can be applied simultaneously together or separately or in succession, the sequence, in the case of separate application, generally not having any effect on the result of the control measures.

The compounds I and II are usually used in a weight ratio of 200:1 to 0.1:1, preferably 100:1 to 1:1, in particular 50:1 to 5:1 (II:I).

The compounds I and III are usually used in a weight ratio of 10:1 to 0.1:1, preferably 5:1 to 0.2:1, in particular 3:1 to 1:3 (III:I).

The application rates of the mixtures according to the invention are, in the case of the compounds I, in general from 0.005 to 0.5 kg/ha, preferably 0.01 to 0.5 kg/ha, in particular 0.01 to 0.3 kg/ha, depending on the nature of the desired effect.

The application rates for the compounds II are in general from 0.1 to 10 kg/ha, preferably 0.5 to 5 kg/ha, in particular 1 to 4 kg/ha.

The application rates for the compound III are as a rule from 0.005 to 0.8 kg/ha, preferably 0.01 to 0.5 kg/ha, in particular 0.05 to 0.3 kg/ha.

For seed treatment, the application rates of the mixture are generally from 0.001 to 100 g/kg of seed, preferably 0.01 to 50 g/kg, in particular 0.01 to 10 g/kg.

If phytopathogenic harmful fungi are to be controlled, the separate or joint application of the compounds I and II or III or of the mixtures of the compounds I, II and III is effected by spraying or dusting the seeds, the plants or the soils before or after sowing of the plants, or before or after plant emergence.

The fungicidal synergistic mixtures according to the invention, or the compounds I, II and III, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or jointly grinding the compounds I, II and/or III or the mixture of the compounds I, II and III with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of the compounds I, II and/or III or of the mixture of the compounds I, II and III. The active ingredients are employed in a purity of from 90% to 100%, preferably 95% to 100% (according to NMR or HPLC spectrum).

The compounds I, II and/or III, or the mixtures, or the corresponding formulations, are applied by treating the harmful fungi or the plants, seeds, soils, areas, materials or spaces to be kept free from them with a fungicidally active amount of the mixture, or of the compounds I, II and/or III in the case of separate application. Application can be effected before or after infection by the harmful fungi.

Examples of the synergistic action of the mixtures according to the invention against harmful fungi.

The fungicidal action of the compound and of the mixtures is demonstrated by the following experiments:

The active ingredients, separately or together, are formulated as a 10% emulsion in a mixture of 70% by weight of cyclohexanone, 20% by weight of Nekanil® LN (Lutensol® AP6, wetting agent having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

Evaluation takes place by determining the infected leaf areas in percent. These percentages are converted into degrees of action. The expected degrees of action of the mixtures of the active ingredients are determined using Colby's formula [R. S. Colby, Weeds 15, 20–22 (1967)] and compared with the observed degrees of action.
Colby's formula:

$$E = x + y + z - x \cdot y \cdot z / 100$$

E expected degree of action, expressed in % of the untreated control, when using the mixture of the active ingredients A, B and C at the concentrations a, b and c x degree of action, expressed in % of the untreated control, when using active ingredient A at a concentration of a y degree of action, expressed in % of the untreated control, when using active ingredient B at a concentration of b z degree of action expressed in % of the untreated control, when using active ingredient C at a concentration of c The efficacy (E) is calculated as follows using Abbot's formula:

$$E = (1-\alpha) \cdot 100/\beta$$

α corresponds to the fungal infection of the treated plants in % and

β corresponds to the fungal infection of the untreated (control) plants in %

A degree of action of 0 means that the infection level of the treated plants corresponds to that of the untreated control plants; a degree of action of 100 means that the treated plants are not infected.

EXAMPLES 1–14

Activity Against *Plasmopara viticola*

Leaves of potted vines of the variety "Müller-Thurgau" were sprayed with an aqueous active compound preparation prepared from a stock solution of 10% of active compound, 63% of cyclohexanone and 27% of emulsifier until dripping wet. To be able to assess the long-term activity of the substances, the plants were kept for 7 days in the greenhouse after the spray coating had dried on. Only then were the leaves inoculated with an aqueous zoospore suspension of *Plasmopara viticola*. The vines were then first kept in a chamber saturated with water vapor at 24° C. for 48 hours, and then in a greenhouse at 20–30° C. for 5 days. The plants were then kept for a further 16 hours in a chamber of high atmospheric humidity to stimulate sporulation of the fungus. The extent of the infection at the undersides of the leaves was then assessed visually.

TABLE 3

| Ex. | Active compound | Concentration of active compound in the spray liquor in ppm | Degree of action in % of the untreated control |
|---|---|---|---|
| 1V | Controll (un-treated) | (99% infestation) | 0 |
| 2V | A = Tab. 1A, No. I.2 | 25 | 74 |
|  |  | 10 | 0 |
|  |  | 5 | 0 |
| 3V | B = Tab. 1A, No. I.4 | 5 | 74 |
| 4V | II b = Maneb | 100 | 0 |
|  |  | 50 | 0 |
|  |  | 25 | 0 |
| 5V | IIc = Metiram | 100 | 74 |
|  |  | 50 | 48 |

TABLE 4

| Ex. | Concentration of active compound in the spray liquor in ppm | Observed degree of action | Calculated degree of action*) |
|---|---|---|---|
| 6 | 10A + 100 IIh | 100 | 0 |
| 7 | 5A + 50 IIb | 100 | 0 |
| 8 | 10A + 50 IIb | 92 | 0 |
| 9 | 5A + 25 IIb | 92 | 0 |
| 10 | 25A + 25 IIb | 95 | 74 |
| 11 | 10A + | 100 | 74 |

TABLE 4-continued

| Ex. | Concentration of active compound in the spray liquor in ppm | Observed degree of action | Calculated degree of action*) |
|---|---|---|---|
| 12 | 100 IIc 10A + 50 IIc | 100 | 48 |
| 13 | 5A + 50 IIb | 92 | 74 |
| 14 | 5B + 50 IIc | 95 | 86 |

*Calculated by the method of Colby

EXAMPLES 15–33

Activity against Phytophthora infestans in tomatoes

Leaves of potted plants of the variety "Große Fleischtomate" were sprayed with an aqueous suspension prepared from a stock solution of 10% of active compound, 63% of cyclohexanone and 27% of emulsifier until dripping wet. The following day, the leaves were infected with an aqueous zoospore suspension of Phytophthora infestans. The plants were then placed in a chamber saturated with water vapor at 16–18° C. After 6 days, the tomato blight on the infected untreated control plants had developed to such an extent that the infestation could be assessed visually in %.

TABLE 5

| Ex. | Active compound | Concentration of active compound in the spray liquor in ppm | Degree of action in % of the untreated control |
|---|---|---|---|
| 15V | Control (untreated) | (99% infestation) | 0 |
| 16V | B = Tab. 1A, No. I.2 | 20 | 88 |
|  |  | 10 | 0 |
|  |  | 5 | 0 |
| 17V | B = Tab. 1A, No. I.4 | 100 | 74 |
|  |  | 20 | 65 |
|  |  | 10 | 65 |
|  |  | 5 | 0 |
| 18V | II b = Maneb | 100 | 0 |
|  |  | 50 | 0 |
|  |  | 25 | 0 |
| 19V | IIc = Metiram | 500 | 93 |

TABLE 6

| Ex. | Concentration of active compound in the spray liquor in ppm | Observed degree of action | Calculated degree of action*) |
|---|---|---|---|
| 20 | 10A + 100 IIb | 100 | 0 |
| 21 | 5A + 50 IIb | 100 | 0 |
| 22 | 20A + 100 IIb | 100 | 88 |
| 23 | 10A + 50 IIb | 77 | 0 |
| 24 | 5A + 25 IIb | 77 | 0 |
| 25 | 5A + 50 IIb | 100 | 93 |
| 26 | 10A + 50 IIc | 100 | 93 |
| 27 | 10B + 100 IIb | 100 | 65 |

TABLE 6-continued

| Ex. | Concentration of active compound in the spray liquor in ppm | Observed degree of action | Calculated degree of action*) |
|---|---|---|---|
| 28 | 5B + 50 IIb | 100 | 0 |
| 29 | 20B + 100 IIb | 100 | 65 |
| 30 | 10B + 50 IIb | 100 | 65 |
| 31 | 5B + 25 IIb | 77 | 0 |
| 32 | 100B + 100 IIb | 100 | 74 |
| 33 | 5B + 50 IIc | 100 | 93 |

EXAMPLES 34–40

Curative Action Against *Plasmopara viticola*

Leaves of potted vines of the variety "Müller-Thurgau" were inoculated with an aqueous zoospore suspension of *Plasmopara viticola*. The vines were then kept at 22–24° C. in a chamber saturated with water vapor for 48 hours. They were then removed from the chambers and, after drying, sprayed with an aqueous active compound preparation prepared from a stock solution of 10% of active compound, 63% of cyclohexanone and 27% of emulsifier until dripping wet. After the spray coating had dried on, the plants were further cultivated in the greenhouse at 20–30° C. for 5 days. The plants were then kept for a further 16 hours in a climatized chamber of high atmospheric humidity to stimulate sporulation of the fungus. The extent of the infection at the undersides of the leaves was then assessed visually.

TABLE 7

| Ex. | Active compound | Concentration of active compound in the spray liquor in ppm | Degree of action in % of the untreated control |
|---|---|---|---|
| 34V | Control (untreated) | (99% infestation) | 0 |
| 35V | A = Tab. 1A, No. I.2 | 25 | 19 |
|  |  | 12.5 | 0 |
| 36V | B = Tab. 1A, No. I.4 | 12.5 | 0 |
| 37V | III = Cymoxanil | 25 | 90 |
|  |  | 12.5 | 60 |

TABLE 8

| Ex. | Concentration of active compound in the spray liquor in ppm | Observed degree of action | Calculated degree of action*) |
|---|---|---|---|
| 38 | 25A + 25 III | 100 | 92 |
| 39 | 12.5A + 12.5 III | 80 | 60 |
| 40 | 12.5B + 12.5 III | 80 | 60 |

*)Calculated by the method of Colby

The results from the examples demonstrate that at all mixing ratios the observed degree of action is higher than the degree of action calculated by the Colby formula.

What is claimed is:

1. A fungicidal comprising synergistically effective amounts of a) an oxime ether I

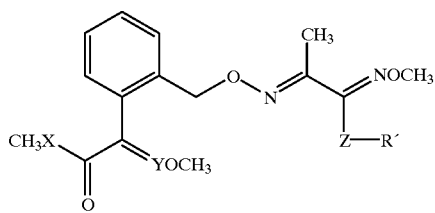
(I)

wherein the substituents have the following meaning:
X is oxygen or amino (NH);
Y is CH or N;
Z is oxygen, sulfur, amino (NH) or $C_1$–$C_4$-alkylamino (N—$C_1$–$C_4$-alkyl);
R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or benzyl which may be partially or fully halogenated and/or may carry one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

and b) a dithiocarbamate (II) selected from the group consisting of
manganese ethylenebis(dithiocarbamate) (zinc complex) (IIa),
manganese ethylenebis(dithiocarbamate) (IIb),
zinc ammoniate ethylenebis(dithiocarbamate) (IIc) and
zinc ethylenebis(dithiocarbamate) (IId).

2. The fungicidal composition defined in claim 1, wherein the dithiocarbamate (II) is manganese ethylenebis (dithiocarbamate) (zinc complex) (IIa).

3. The fungicidal composition defined in claim 1, wherein the dithiocarbamate (II) is manganese ethylenebis (dithiocarbamate) (IIb).

4. The fungicidal composition defined in claim 1, wherein the dithiocarbamate (II) is zinc ammoniate ethylenebis (dithiocarbamate) (IIc).

5. The fungicidal composition defined in claim 1, wherein the dithiocarbamate (II) is zinc ethylenebis(dithiocarbamate) (IId).

6. The fungicidal composition defined in claim 1, further comprising 1-(2-cyano-2-methoxyiminoacetyl)-3-ethylurea (III).

7. The fungicidal composition defined in claim 1, wherein the weight ratio of the dithiocarbamate (II) to the oxime ether I is from 200:1 to 0.1:1.

8. A method of controlling harmful fungi, which comprises treating the harmful fungi, their environment, or the plants, seeds, soils, areas, materials or spaces to be kept free from said fungi with syneraistically effective amounts of an oxime ether I and a dithiocarbamate (II) as set forth in claim 1.

9. The method defined in claim 8, wherein the oxime ether I is applied in an amount of from 0.005 to 0.5 kg/ha.

10. The method defined in claim 8, wherein the dithiocarbamate (II) is applied in an amount of from 0.1 to 10 kg/ha.

11. The fungicidal composition defined in claim 6, wherein the dithiocarbamate (II) is manganese ethylenebis (dithiocarbamate) (zinc complex) (IIa).

12. The fungicidal composition defined in claim 6, wherein the dithiocarbamate (II) is manganese ethylenebis (dithiocarbamate) (IIb).

13. The fungicidal composition defined in claim 6, wherein the dithiocarbamate (II) is zinc ammoniate ethylenebis(dithiocarbamate) (IIc).

14. The fungicidal composition defined in claim 6, wherein the dithiocarbamate (II) is zinc ethylenebis (dithiocarbamate) (IId).

15. The fungicidal composition defined in claim 6, wherein the weight ratio of the dithiocarbamate (II) to the oxime ether I is from 200:1 to 0.1:1.

16. The fungicidal composition defined in claim 6, wherein the weight ratio of the 1-(2-cyano-2-methoxyiminoacetyl)-3-ethylurea (III) to the oxime ether I is from 10:1 to 0.1:1.

17. The method defined in claim 8, further comprising treating the harmful fungi, their environment, or the plants, seeds, soils, areas, materials or spaces to be kept free from said fungi with a synergistically effective amount of 1-(2-cyano-2-methoxyiminoacetyl)-3-ethylurea (III).

18. The method defined in claim 17, wherein the oxime ether I is applied in an amount of from 0.005 to 0.5 kg/ha.

19. The method defined in claim 17, wherein the dithiocarbamate (II) is applied in an amount of from 0.1 to 10 kg/ha.

20. The method defined in claim 17, wherein 1-(2-cyano-2-methoxyiminoacetyl)-3-ethylurea (III) is applied in an amount of from 0.005 to 0.8 kg/ha.

* * * * *